United States Patent [19]

Nakagawa et al.

[11] 4,086,360
[45] Apr. 25, 1978

[54] PHENYL THIOL CARBANILIDE DERIVATIVES, METHOD FOR THE PREPARATION THEREOF AND USE THEREOF AS FUNGICIDE FOR AGRICULTURE

[75] Inventors: Taizo Nakagawa, Ageo; Kaoru Ohmori, Okegawa; Yutaka Watanabe, Saitama; Iwao Tejima, Ageo; Shuichi Ishida, Omiya; Toshiyuki Suzuki; Osamu Yamada, both of Ageo, all of Japan

[73] Assignee: Nippon Kayaku Kabushiki Kaisha, Tokyo, Japan

[21] Appl. No.: 691,602

[22] Filed: Jun. 1, 1976

[30] Foreign Application Priority Data

Jun. 11, 1975 Japan .................. 50-70304

[51] Int. Cl.$^2$ ................ A01N 9/12; C07C 155/02
[52] U.S. Cl. ........................... 424/300; 260/455 A
[58] Field of Search ............... 260/455 A; 424/300

[56] References Cited

U.S. PATENT DOCUMENTS

| 3,404,975 | 10/1968 | Wilson et al. | 260/455 A |
| 3,450,745 | 6/1969 | Payne et al. | 260/455 A |
| 3,719,702 | 3/1973 | Traber et al. | 424/300 |
| 3,832,374 | 8/1974 | Liebig et al. | 260/455 A |

FOREIGN PATENT DOCUMENTS 1,337,797  6/1962  France ................ 260/455 A

*Primary Examiner* — Delbert R. Phillips
*Attorney, Agent, or Firm* — Russell & Nields

[57] ABSTRACT

New phenyl thiol carbanilide derivatives of the present invention are represented by the formula

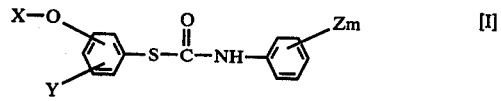

where X represents a lower alkylsulfonyl, a lower alkoxycarbonyl, a N-lower alkylcarbamoyl, a lower alkylcarbonyl or an O,O-dilower alkyl thiophosphonyl, Y represents hydrogen, chlorine, bromine or a lower alkyl, Z represents hydrogen, fluorine, chlorine, bromine, a lower alkyl, a lower alkoxy or trifluoromethyl and $m$ represents 1 or 2. The compounds have excellent fungicidal activity against fungi which cause diseases of plants.

6 Claims, No Drawings

4,086,360

PHENYL THIOL CARBANILIDE DERIVATIVES, METHOD FOR THE PREPARATION THEREOF AND USE THEREOF AS FUNGICIDE FOR AGRICULTURE

BACKGROUND OF THE INVENTION

The compound

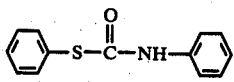

is known by CA. Vol. 48, 10634e (1954) and it is known that the esters of thiocarbamic acid such as

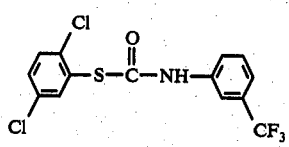

have anthelmintic activity by CA. Vol. 67, 21618f (1967). However, the present compounds are new compounds which are not shown in the prior art. And there is no prior art which suggests that the present compounds have excellent fungicidal activity against fungi which harm useful plants and crops.

DETAILED DESCRIPTION OF THE INVENTION

The present invention relates to new phenylthiol carbanilide derivatives of the formula

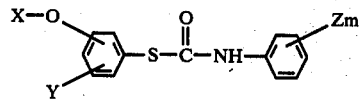

where X represents a lower alkylsulfonyl, a lower alkoxycarbonyl, a N-lower alkylcarbamoyl, a lower alkylcarbonyl or an 0.0-dilower alkyl thiophosphonyl, Y represents hydrogen, chlorine, bromine and a lower alkyl, Z represents hydrogen, fluorine, chlorine, bromine, a lower alkyl, a lower alkoxy or trifluoromethyl and m represents 1 or 2, the method for the preparation thereof, fungicidal composition for agriculture and the method for killing fungi which harm agricultural plants or crops.

The terms "lower alkyl" and "lower alkoxy" in the present invention means, respectively, an alkyl or alkoxy having 1-6 carbon atoms. The present compounds are prepared by method A or method B as shown in the following reaction formulas.

Method A

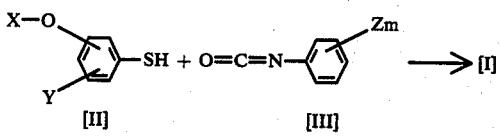

Method B

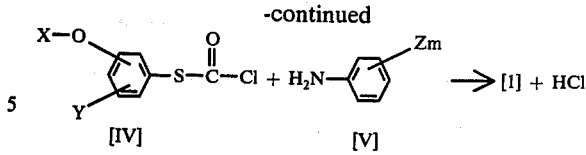

In the case of method A, the thiophenol represented by the formula [II] is reacted with the phenylisocyanate represented by the formula [III] in an inactive organic solvent, preferably, in the presence of a tertiary amine such as triethylamine in an amount of 0.01 - 1% (molar ratio) of the amount of the compound of the formula [II].

The reaction temperature is usually more than 0° C, preferably between room temperature and the boiling point of the inactive organic solvent.

The preferred molar ratio of the thiophenol represented by the formula [II] : the phenylisocyanate represented by the formula [III] is 1 : 0.9 - 1.1.

The preferred inactive solvents used by method A are aliphatic or aromatic hydrocarbons which may be substituted by halogen atoms, for example, chloroform, carbon tetrachloride, cyclohexane, benzene, toluene, xylene and chlorobenzene; ketones such as acetone and methylisobutylketone; esters of acetic acid such as ethyl acetate and butyl acetate; aliphatic nitrils such as acetonitrile and propionitrile and ethers such as diethylether, tetrahydrofuran and dioxane. The thiophenols of the formula [II] are for example, 4-methane sulfonyloxy benzene thiol (white crystals, m.p. 67°-68° C), 4-ethane sulfonyloxy benzene thiol (colorless transparent liquid, $n_D^{25}$ 1.5602), 4-n-propane sulfonyloxy benzene thiol (colorless transparent liquid, $n_D^{25}$ 1.5518), 2-brom-4-methane sulfonyloxy benzene thiol (white crystals, m.p. 46.5°-47° C), 3-methane sulfonyloxy benzene thiol (colorless transparent liquid, b.p. 135°-140° C/2 mmHg), 2-methyl-5-methane sulfonyloxy benzene thiol (pale yellow crystals, m.p. 61°-62° C), 2-chloro-5-methane sulfonyloxy benzene thiol (white crystals, m.p. 64°-64.5° C), 2-methane sulfonyloxy-5-chlorobenzene thiol (colorless transparant liquid, b.p. 147°-149° C/2 mmHg), 4-methoxy carbonyloxy benzene thiol, 4-ethoxy carbonyloxy benzene thiol, 4-(N-methylcarbamoyloxy) benzene thiol (pale yellow crystals, m.p. 99°-99.5° C), 4-(0,0-dimethylthiophosphonyl) benzene thiol (colorless transparent liquid, $n_D^{25}$ 1.5675), 4-acetoxy benzene thiol and isopropyl carbonyloxy thiol (colorless transparent liquid, $n_D^{25}$ 1.5347).

These thiophenols are prepared by the known method, for example, by reducing benzene sulfonyl chloride of the formula

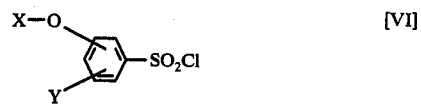

or the benzene disulfide of the formula

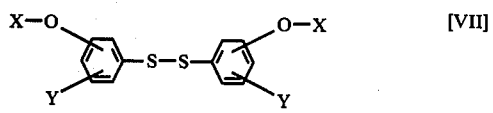

with zinc and mineral acid such as hydrochloric acid in an aqueous solution of an alcohol.

The phenylisocyanates of the formula [III] are, for example, phenylisocyanate, fluoro phenylisocyanate, chlorophenylisocyanate, bromo phenylisocyanate, dichlorophenylisocyanate, tolylisocyanate and methoxyphenylisocyanate.

In the case of Method B, the chlorothio carbonic acid -s-phenyl ester of the formula [IV] is reacted with the aniline of the formula [V] in an inactive organic solvent or a mixture of water and an inactive organic solvent, preferably, in the presence of the base for example a hydroxide of an alkalimetal such as sodium hydroxide, a hydroxide of an alkaline earth metal such as calcium hydroxide, a carbonate of an alkalimetal such as sodium carbonate and potassium carbonate, a bicarbonate such as sodium bicarbonate, an aliphatic tertiary amine such as triethylamine, an aromatic tertiary amine such as dimethylaniline and heterocyclic tertiary amine such as pyridine to obtain the compound of the formula [I].

The preferred molar ratio a chloro thio carbonic acid-s-phenylester of the formula [IV]: an aniline of the formula [V] is 1 : 1 – 2.2.

The chlorothiocarbonic acid-s-phenyl esters are for example chlorothio carbonic acid-s-(4-methane sulfonyloxyphenyl) ester, chlorothiocarbonic acid-s-(4-ethane sulfonyloxy phenyl) ester, chlorothio carbonic acid-s-(4-n-propanesulfonyloxyphenyl) ester, chlorothiocarbonic acid-s-(3-methane sulfonyloxyphenyl) esters, chloro thio carbonic acid-s-(2-methyl-5-methane sulfonyloxy phenyl) ester, chlorothio carbonic acid-s-(2-chloro-5-methane sulfonyloxy phenyl) ester, chloro thio phenyl carbonic acid-s-(2-methane sulfonyloxy-5-chloro phenyl) ester, chloro thio carbonic acid-s-(4-methoxy carbonyloxy phenyl) ester, chloro thio carbonic acid-s-(4-ethoxy carbonyloxy phenyl) ester, chlorothio carbonic acid-s-(4-N-methyl carbamoyloxy phenyl) ester and chlorothio carbonic acid-s-(4-0,0-dimethylthiophosphoryl phenyl) ester, chlorothio carbonic acid-s-(4-acetoxy phenyl) ester. These chloro thio carbonic acid -s-phenyl esters are obtained by reacting the thiophenol of the formula [II] with phosgene, preferably, in the presence of the base in an inactive organic solvent. The anilines of the formula [V] are, for example, aniline, fluoro aniline, chloro aniline, bromo aniline, dichloro aniline, toluidine, xylidine, anisidine, phenethidine and aminobenzo trifluoride.

The methods for the preparation of the present compounds are shown by the following preparation examples.

PREPARATION EXAMPLE 1

The preparation of

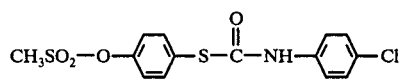

(Compound 7) by Method A

Seven grams (7 g) (0.0343 mole) of 4-methane sulfonyloxy benzene thiol and 5.3 g (0.0345 mole) of 4-chlorophenyl isocyanate were dissolved in 70 ml of benzene. One drop of triethylamine was added to the resultant solution and the solution maintained at room temperature till the reaction was completed. Crystals precipitated were filtered and recrystalied from benzene. Eleven point four grams (11.4 g) of the white crystals were obtained.

Yields: 92.9%, m.p. 150°–152° C.

Elemental analysis for $C_{14}H_{12}ClNO_4S_2$: Found C; 47.10%, H; 3.26%, N; 3.99%. Calculated C; 46.99%, H; 3.38%, N; 3.92%.

PREPARATION EXAMPLE 2

The preparation of

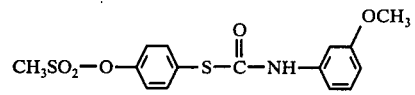

(Compound No. 6) by the Method B

Eight point nine grams (8.9 g) (0.072 mole) of m-anisidine were dissolved in 80 ml of ethylacetate and 50 ml of water mixed to the solution. Eight grams (8.0 g) (0.030 mole) of chlorothio carbonic acid-s-(4-methane sulfonyloxy phenyl) ester were added dropwise to the mixture with stirring and then stirring was continued for 3 hours at 20°–25° C.

After stirring, a layer of ethylacetate was separated from the mixture and washed with successive, 5%-hydrochloric acid aqueous solution, 5%-sodium hydroxide aqueous solution and water. Anhydrous sodium sulfate was added to the layer of ethylacetate to remove water from the layer.

Ethyl acetate was removed by the distillation and crude crystals were obtained. The crude crystals were recrystallized from benzene and 7.5 g of white crystals were obtained.

Yields: 70.7% m.p. 121°–122° C.

Elemental analysis for $C_{15}H_{15}N_5S_2$: Founds C; 50.94%, H; 4.36%, N; 3.88%. Calculated C; 50.98%, H; 4.28%, N; 3.96%.

The representative compounds of the present compounds are shown in Table 1.

These compounds were prepared by Method A or Method B. However, these compounds can be prepared by both Methods.

Table 1

| Compound No. | Compound | m.p. ° C | The method used for preparation |
| --- | --- | --- | --- |
| 1 | CH₃SO₂—O—⟨ ⟩—S—C(=O)—NH—⟨ ⟩—OCH₃ | (151–152) | B |
| 2 | CH₃SO₂—O—⟨ ⟩—S—C(=O)—NH—⟨ ⟩—CH₃ | (147–148) | " |

Table 1-continued

| Compound No. | Compound | m.p. °C | The method used for preparation |
|---|---|---|---|
| 3 | CH₃SO₂—O—⟨C₆H₄⟩—S—C(=O)—NH—⟨C₆H₄⟩—CH₃ (m) | (133–134) | " |
| 4 | CH₃SO₂—O—⟨C₆H₄⟩—S—C(=O)—NH—⟨C₆H₅⟩ | (130–132) | A |
| 5 | CH₃SO₂—O—⟨C₆H₄⟩—S—C(=O)—NH—⟨C₆H₄⟩—F | (140–141.5) | B |
| 6 | CH₃SO₂—O—⟨C₆H₄⟩—S—C(=O)—NH—⟨C₆H₄⟩—OCH₃ (m) | (121–122) | " |
| 7 | CH₃SO₂—O—⟨C₆H₄⟩—S—C(=O)—NH—⟨C₆H₄⟩—Cl | (150–152) | A |
| 8 | CH₃SO₂—O—⟨C₆H₄⟩—S—C(=O)—NH—⟨C₆H₄⟩—Cl (m) | (140–142.5) | A |
| 9 | CH₃SO₂—O—⟨C₆H₄⟩—S—C(=O)—NH—⟨C₆H₄⟩—Cl (o) | (114–116) | " |
| 10 | CH₃SO₂—O—⟨C₆H₄⟩—S—C(=O)—NH—⟨C₆H₄⟩—Br | (161–162) | B |
| 11 | CH₃SO₂—O—⟨C₆H₄⟩—S—C(=O)—NH—⟨C₆H₄⟩—CF₃ (m) | (116–117) | " |
| 12 | CH₃SO₂—O—⟨C₆H₄⟩—S—C(=O)—NH—⟨C₆H₃⟩(Cl)(Cl) (3,4) | (141–142.5) | A |
| 13 | C₂H₅SO₂—O—⟨C₆H₄⟩—S—C(=O)—NH—⟨C₆H₅⟩ | (89.5–90.5) | " |
| 14 | η-C₃H₇SO₂—O—⟨C₆H₄⟩—S—C(=O)—NH—⟨C₆H₅⟩ | (131–132.5) | " |
| 15 | η-C₃H₇SO₂—O—⟨C₆H₄⟩—S—C(=O)—NH—⟨C₆H₄⟩—F | (105–105.5) | B |
| 16 | η-C₃H₇SO₂—O—⟨C₆H₄⟩—S—C(=O)—NH—⟨C₆H₄⟩—OCH₃ (m) | (98–99) | " |
| 17 | CH₃SO₂—O—⟨C₆H₄⟩(m)—S—C(=O)—NH—⟨C₆H₄⟩—Cl | (108–109) | A |
| 18 | CH₃SO₂—O—⟨C₆H₄⟩(m)—S—C(=O)—NH—⟨C₆H₄⟩—Cl (m) | (133–135) | " |
| 19 | CH₃SO₂—O—⟨C₆H₄⟩(m)—S—C(=O)—NH—⟨C₆H₅⟩ | (84–85) | A |
| 20 | CH₃SO₂—O—⟨C₆H₃⟩(CH₃)—S—C(=O)—NH—⟨C₆H₅⟩ | (135–137) | " |

Table 1-continued

| Compound No. | Compound | m.p. °C | The method used for preparation |
|---|---|---|---|
| 21 | CH₃SO₂—O—⟨benzene, Cl⟩—S—C(=O)—NH—⟨benzene, 3-Cl⟩ | (120–121) | " |
| 22 | CH₃SO₂—O—⟨benzene, Cl⟩—S—C(=O)—NH—⟨benzene, 4-Cl⟩ | (153–156) | " |
| 23 | ⟨benzene, O—SO₂CH₃; Cl⟩—S—C(=O)—NH—⟨phenyl⟩ | (96–98) | " |
| 24 | ⟨benzene, O—SO₂CH₃; Cl⟩—S—C(=O)—NH—⟨benzene, CH₃⟩ | (119–121) | B |
| 25 | ⟨benzene, O—SO₂CH₃; Cl⟩—S—C(=O)—NH—⟨benzene, OCH₃⟩ | (119–120) | " |
| 26 | CH₃O—C(=O)—O—⟨benzene⟩—S—C(=O)—NH—⟨phenyl⟩ | (110–111) | A |
| 27 | CH₃O—C(=O)—O—⟨benzene⟩—S—C(=O)—NH—⟨benzene, Cl⟩ | (161–163) | " |
| 28 | CH₃O—C(=O)—O—⟨benzene⟩—S—C(=O)—NH—⟨benzene, CH₃⟩ | (129.5–130.5) | B |
| 29 | CH₃O—C(=O)—O—⟨benzene⟩—S—C(=O)—NH—⟨benzene, OCH₃⟩ | (133–134) | " |
| 30 | C₂H₅O—C(=O)—O—⟨benzene⟩—S—C(=O)—NH—⟨phenyl⟩ | (91–92) | A |
| 31 | C₂H₅O—C(=O)—O—⟨benzene⟩—S—C(=O)—NH—⟨benzene, Cl⟩ | (86–87) | " |
| 32 | C₂H₅O—C(=O)—O—⟨benzene⟩—S—C(=O)—NH—⟨benzene, Cl⟩ | (112–112.5) | A |
| 33 | C₂H₅O—C(=O)—O—⟨benzene⟩—S—C(=O)—NH—⟨benzene, Cl⟩ | (127.5–128.5) | " |
| 34 | CH₃—NH—C(=O)—O—⟨benzene⟩—S—C(=O)—NH—⟨phenyl⟩ | (159–160) | " |
| 35 | CH₃—NH—C(=O)—O—⟨benzene⟩—S—C(=O)—NH—⟨benzene, Cl⟩ | (190–191) | A |
| 36 | (CH₃O)₂P(=S)—O—⟨benzene⟩—S—C(=O)—NH—⟨phenyl⟩ | (79.5–81.5) | " |
| 37 | (CH₃O)₂P(=S)—O—⟨benzene⟩—S—C(=O)—NH—⟨benzene, Cl⟩ | (90–91) | " |
| 38 | CH₃—C(=O)—O—⟨benzene⟩—S—C(=O)—NH—⟨phenyl⟩ | (109–111) | " |

Table 1-continued

| Compound No. | Compound | m.p. °C | The method used for preparation |
|---|---|---|---|
| 39 | CH$_3$—C(=O)—O—⟨ph⟩—S—C(=O)—NH—⟨ph⟩—Cl | (149–150) | " |
| 40 | (CH$_3$)$_2$CH—C(=O)—O—⟨ph⟩—S—C(=O)—NH—⟨ph⟩—Cl | (122–124) | " |
| 41 | CH$_3$SO$_2$—O—⟨ph(Br)⟩—S—C(=O)—NH—⟨ph⟩ | (178–179) | " |
| 42 | CH$_3$—C(=O)—O—⟨ph⟩—S—C(=O)—NH—⟨ph⟩—OCH$_2$CH$_3$ | (125–126) | B |

A preferred compound is a compound of the formula [I] where X represents an alkylsulfonyl where an alkyl has from 1 to 3 carbon atoms, methoxy carbonyl, acetyl or an O,O-dimethyl thiosulfonyl, Y represents hydrogen or chlorine, Z represents hydrogen, p-fluorine, p-chlorine, p-bromine or methoxy and m represents 1. These compounds have especially a superior fungicidal activity.

The present compounds exhibited excellent fungicidal activity against fungi which cause the diseases of many useful plants. The representative plant diseases which are prevented by the application of the present compounds are as follows:

Rice plant diseases, for example, rice blast of rice plant caused by *Pyricularia oryzae*, and Helminthosporium leaf spot of rice plant caused by *Cochliobolus miyabeanus*, vegetable diseases, for example, downy mildew of cucumber caused by *Pseudoperonospora cubensis*, powdery mildew of cucumber caused by *Sphaerotheca fuliginea*, anthracnose fo cucumber caused by *Colletotrichum lagenarium* and cucumber scab caused by *Cladosporium cucumerinum* and fruit crop diseases, for example, black spot of Japanese pear caused by *Alternaria kikuchiana*, ripe rot of grape caused by *Glomerella cingulata*, brown rot of peach caused by *Sclerotinia laxa*, melanose of citrus tree caused by *Diaporthe citri*, common green mold of citrus tree caused by *Penicillium digitatum* and black rot of citrus tree caused by *alternaria citri*.

These plant diseases are prevented by applying an effective amount of the present compounds to fungi which cause these plant diseases. The present compounds, themselves may be directly applied to said fungi which cause many plant diseases. However, in general, one or more of the compounds are mixed with suitable adjuvants and formed into fungicidal compositions such as an emulsifiable concentration, a wettable powder, a water-soluble concentration, a dust, granules and pellets and used.

The amount of the compounds contained in the composition may be varied depending upon the method of application or kinds of crops of plant on which the composition is to be applied, but it is generally 1–95%, preferably 2 to 90% by weight and the amount of adjuvants is 99–5% preferably 98–10%. The adjuvants used in the present invention include all the substances other than effective compounds, which substances are added so as to enhance, maintain and increase the effect of power of the active compound or to dilute the concentration of the active compound. The adjuvants are, for example, various kinds of carriers and surface active agents. The carriers in the form of solid are, for example, clay, kaolin, talc, diatomaceous earth, silica, calcium carbonate or the like.

The carriers in the form of liquid are benzene, alcohols, acetone, xylene, methylnaphthalene, cyclohexanone, dimethylformamide, dimethylsulfoxide, animal and vegetable oils, fatty acids and their esters, various kinds of surfactants, etc.

It is also possible to enhance the effect by appropriately mixing the active compounds or the mixture of the compounds and carriers with auxiliary substances usually employed for agricultural preparations, such as an extending agent, an emulsifier, a wetting agent and a binding agent. The present compounds may also be used in admixture with other agricultural fungicides, insecticides, herbicides, plant growth regulators, soil modifying agents or fertilizers. When the composition in the form of a wettable powder, a water-soluble concentration or an emulsifiable concentration is practically applied to fungi which harm agricultural and horticultural plants or crops, it may preferably be diluted with water so that the present compounds are contained in an amount of about 25 – 8000 ppm, preferably 50 – 2000 ppm.

In the form of a dust, pellets or granules, the present compound is used in an amount of 0.30 kg – 1 kg/10 ares. For the soil treatment, preferably, the present compound is used in the form of a dust, granules or pellets and the compound preferably is applied in an amount of 0.05 kg – 2 kg/10 ares. When the compound is used for seed treatment, the seeds are dipped into the diluted solution in which the compound is contained in an amount of about 0.05 – 1.0% or seeds are dressed with a dust in which the compound is contained. The amount of the compound dressed is 0.1 – 5% of seed weight.

The compositions and effects of the present invention will be explained more in detail by following examples. Parts used in composition Examples are parts by weight.

COMPOSITION EXAMPLE 1

Dust

Three parts of compound No. 1, 48 parts of talc and 49 parts of clay were uniformly mixed and crushed to give a dust. The dust was sprayed over crops and plants, applied to soil and mixed with seeds and/or tubers.

The each dust containing Compound No. 6, No. 7, No. 16, No. 25, No. 29 or No. 36 was prepared by the same method.

COMPOSITION EXAMPLE 2

Wettable Powder

Eighty parts of compounds No. 29, 15 parts of kaolin, 3 parts of sodium alkylbenzenesulfonate and 2 parts of sodium polyacrylic acid were uniformly mixed and crushed to give a wettable powder. The wettable powder was suspended into water and used as spraying liquid. The each wettable powder containing a compound shown in Table 1 except compound No. 29 was prepared by the same method.

COMPOSITION EXAMPLE 3

Granules

Three parts of compound No. 7, 35 parts of diatomaceous earth, 23 parts of bentonite, 37 parts of talc and 2 parts of disintegrator were uniformly mixed and 18 parts of water added. The mixture was blended to become uniformly wet and formed into granules by means of a granulating machine having a sieve of 0.6 mm to 1.0 mm and the wet granules were dried to obtain dry granules. The granules were sprayed to crops and plants and applied to soil.

COMPOSITION EXAMPLE 4

Emulsifiable Concentration

Twenty parts of compound No. 36 were dissolved into 63 parts of xylene. Seventeen parts of the mixture of calcium alkylbenzene sulfonate and the condensation products of alkylphenol and ethylene oxide (the ratio calcium alkylbenzene sulfonate: the condensation product is 2 : 8) were dissolved in the resultant solution to obtain an emulsifiable concentration was diluted with water for form emulsion and the emulsion was used as spraying liquid.

The each emulsifiable concentration containing Compound No. 1, No. 4, No. 6, No. 7, No. 14, No. 15, No. 16, No. 26 or No. 29 was prepared by the same method.

EXPERIMENTAL EXAMPLE 1

Test for prevention of rice blast of rice plant caused by *Pyricularia oryzae*

About 50 seeds of rice plant (variety: *Saitama mochi* No. 10) were sowed in a pot (15 × 5 cm × 10 cm) which was made from polyvinyl chloride. Fifty miligrams of a 3% dust prepared by Composition Example 1 were sprayed on the rice seedlings having 2 - 3 leaves which breeded for 20 days and then small pieces of rice leaves which infected rice blast of rice plant were scattered on the rice seedlings for inoculation of *Pyricularia oryzae*. The degrees attached by the disease were observed at 20th days after inoculation.

Two percents dust of 0.0-di-isopropyl-s-benzyl phosphoro thiolate (hereinafter referred as IBP) and 0.2% dust of kasugamycin as known fungicides were used for comparative tests.

The results are shown in Table 2. Rate of prevention in Table 2 is defined as follows:

$$\text{Rate of prevention} = \frac{\text{Infect index in the untreated area} - \text{Infect index in the treated area}}{\text{Infect index in the untreated area}}$$

Wherein Infected index is defined as follows;

$$\text{Infected index} = \frac{\text{The number of infected leaves by attack of desease}}{\text{The number of all leaves}}$$

Table 2

| Test compounds (Number) | Concentration | Rate of prevention | Phytotoxicity |
|---|---|---|---|
| 1 | 200$^{g/10a}$ | 92% | Nil |
| 6 | 200 | 88 | Nil |
| 7 | 200 | 84 | Nil |
| 16 | 200 | 90 | Nil |
| 25 | 200 | 84 | Nil |
| 29 | 200 | 94 | Nil |
| 36 | 200 | 85 | Nil |
| IBP (2% dust) | 200 | 87 | Nil |
| Kasugamycin (0.2% dust) | 20 | 84 | Nil |
| Untreated | — | 0 | — |

EXPERIMENTAL EXAMPLE 2

Exterminating test on cucumber powdery mildew caused by *Sphaerothoca fuliginea*

The cucumber seedlings (variety: sagamihanjiro) which were sown before one month were transplanted in a green house. One week after transplanting, 80% wettable powder of Composition Example 2 which was diluted with water was sprayed over the cucumber in an amount of 50 ml per plant 5 times at a interval of 5 days. Seventy-five percent wettable powder of tetrachloroisofutaronitril (hereinafter referred as TPN) as known fungicide was used for the standard chemical.

Ten days after the last spraying, degrees of attack by cucumber powdery mildew which was naturally attacked were observed with 7 leaves from the bottom and the results were shown in Table 3 with an "Infected Index". An "Infected Index" was calculated as following $$\text{Infected Index} = \frac{(A \times 4) + (B \times 3) + (C \times 2) + (D \times 1)}{(A+B+C+D+E) \times 4} \times 100$$

A : Number of leaves having more than 80% diseased area
B : Number of leaves having 60 - 70% diseased area
C : Number of leaves having 30 - 59% diseased area
D : Number of leaves having less than 29% diseased area
E : Number of healthy leaves.

Table 3

| Test compounds (Number) | Concentration (ppm) | Infected Index | Phytotoxicity |
|---|---|---|---|
| 1 | 1,000 | 26 | Nil |
| 7 | 1,000 | 29 | Nil |
| 17 | 1,000 | 32 | Nil |
| 19 | 1,000 | 30 | Nil |
| TPN (75% W.P.) | 1,250 | 36 | Nil |
| Untreated | — | 67 | — |

EXPERIMENTAL EXAMPLE 3

Exterminating test on cucumber scab caused by *Cladosporium cucumerinum*

The cucumber seeds (variety : Sagamihanjiro) were sown in 18 cm pots. At the stage of 3 - 4 leaves, 80% wettable powder of Composition Example 2 which was diluted with water were sprayed over the cucumber seedlings in an amount of 20 ml per pot. After 24 hours, the seedlings were inoculated by means of spray with spore suspension of *Cladosporium cucumerinum*. The thus-inoculated seedlings were placed in a moist chamber at 20° C for 24 hours. Then the pot were kept in a green hours at 20° C.

Fifty percent wettable powder of 1,2-bis (3-ethoxy carbonyl-2-thioureid) benzene (hereinafter referred as Thiophanate) and 75% wettable powder of ethylene bis (dithiocarbamic acid) manganese (hereinafter referred as Maneb) as known fungicides were used for the standard chemicals.

Five days after the inoculation, degrees of attack by the pathogen were observed and the results were shown in Table 4 with an "Infected Index". An "Infected Index" was calculated as following $$\text{Infected Index} = \frac{(A \times 3) + (B \times 2) + (C \times 1)}{(A + B + C + D) \times 3} \times 100$$

A : Number of leaves which were dried by hard attack
B : Number of leaves severely attack
C : Number of leaves slightly attack
D : Number of healthy leaves Table 4

| Test compounds (Number) | Concentration (ppm) | Infected Index | Phytotoxicity |
|---|---|---|---|
| 1 | 500 | 3.9 | Nil |
| 2 | 500 | 13.7 | Nil |
| 3 | 500 | 15.2 | Nil |
| 4 | 500 | 7.5 | Nil |
| 5 | 500 | 10.2 | Nil |
| 6 | 500 | 8.6 | Nil |
| 7 | 500 | 5.9 | Nil |
| 8 | 500 | 15.0 | Nil |
| 9 | 500 | 17.2 | Nil |
| 10 | 500 | 8.3 | Nil |
| 11 | 500 | 12.7 | Nil |
| 12 | 500 | 11.9 | Nil |
| 13 | 500 | 12.1 | Nil |
| 14 | 500 | 9.9 | Nil |
| 15 | 500 | 13.1 | Nil |
| 16 | 500 | 13.3 | Nil |
| 17 | 500 | 10.2 | Nil |
| 18 | 500 | 20.3 | Nil |
| 19 | 500 | 15.2 | Nil |
| 20 | 500 | 21.4 | Nil |
| 21 | 500 | 12.0 | Nil |
| 22 | 500 | 14.3 | Nil |
| 23 | 500 | 10.8 | Nil |
| 24 | 500 | 16.9 | Nil |
| 25 | 500 | 9.8 | Nil |
| 26 | 500 | 15.2 | Nil |
| 27 | 500 | 13.7 | Nil |
| 28 | 500 | 19.2 | Nil |
| 29 | 500 | 6.3 | Nil |
| 30 | 500 | 19.2 | Nil |
| 31 | 500 | 13.8 | Nil |
| 32 | 500 | 16.2 | Nil |
| 33 | 500 | 11.7 | Nil |
| 34 | 500 | 15.3 | Nil |
| 35 | 500 | 14.8 | Nil |
| 36 | 500 | 10.2 | Nil |
| 37 | 500 | 9.8 | Nil |
| 38 | 500 | 7.5 | Nil |
| 39 | 500 | 8.2 | Nil |
| 40 | 500 | 9.2 | Nil |
| 41 | 500 | 13.7 | Nil |
| 42 | 500 | 5.2 | Nil |
| Thiophanate (50% W.P.) | 500 | 14.6 | Nil |
| Maneb (75 % W.P.) | 1,500 | 12.5 | Nil |
| Untreated | — | 91.0 | — |

EXPERIMENT EXAMPLE 4

Exterminate test on black spot of Japanese pear caused by *Alternaria kikuchiana*

The Japanese pear seedlings which were planted in 30 cm pots were used in this test. Twenty percent emulsion of Composition Example 4 was diluted with water and sprayed over the seedlings in an amount of 50 ml per pot. Four days after spraying, the leaves of the seedlings were inoculated by means of spray with spore suspension of *Alternaria kikuchiana*, and keep in a moist chamber for 24 hours, then transfered to the green house for developing the disease.

Eighty percent wettable powder which contains N-(1,1,2,2-tetrachloroethylthio)-4-cyclohexene-1,2-dicarboxyimide (hereinafter referred Difolatan) as effective compound was used as a standard chemical and tested by the same method.

Six days after inoculation, degrees of attack by black spot of Japanese pear were observed, and the results were shown in Table 5 with an "Infected Index". The "Infected Index" was calculated as following $$\text{Infected Index} = \frac{(A \times 4) + (B \times 3) + (C \times 2) + (D \times 1)}{(A + B + C + D + E) \times 4} \times 100$$

A : Number of leaves having more than 80% of diseased area
B : Number of leaves having 60-70% of diseased area
C : Number of leaves having 30-59% of diseased area
D : Number of leaves having less than 29% diseased area
E : Number of the healthy leaves Table 5

| Test compounds (Number) | Concentration (ppm) | Infected Index | Phytotoxicity |
|---|---|---|---|
| 1 | 1,000 | 11.7 | Nil |
| 4 | 1,000 | 27.2 | Nil |
| 6 | 1,000 | 22.4 | Nil |
| 7 | 1,000 | 32.0 | Nil |
| 14 | 1,000 | 19.7 | Nil |
| 15 | 1,000 | 30.9 | Nil |
| 16 | 1,000 | 25.5 | Nil |
| 26 | 1,000 | 24.2 | Nil |
| 29 | 1,000 | 12.2 | Nil |
| Difolatan (80% W.P.) | 800 | 26.3 | Nil |
| Untreated | — | 78.1 | — |

EXPERIMENTAL EXAMPLE 5

Exterminate test on Citrus melanose caused by *Diaporthe citri*

The Summer orange seedlings which were planted in 30 cm pot were used in this test.

Eighty percent wettable powder of Compositions Example 2 was diluted with water and sprayed over the seedling in an amount of 50 ml per pot.

Twenty four hours after the spraying, the leaves of the seedlings were inoculated by means of spray with spore suspension of *Diaporthe citri* and kept in a moist chamber at 25° C for 24 hours, then transfered to the green house.

Seventy two percent wettable powder of zinc ethylene bisdithiocarbamate (hereinafter referred as Zineb) as known fungicide was used.

Twenty days after the inoculation, degrees of attack by the pathogen were observed and the results were shown in Table 6 with an "Infected Index". An "Infected Index" was calculated as following $$\text{Infected Index} = \frac{(A \times 5) + (B \times 3) + (C \times 1)}{(A + B + C + D) \times 5} \times 100$$

A : Number of leaves severely attacked
B : Number of leaves moderately attacked

C : Number of leaves slightly attacked
D : Number of healthy leaves.

Table 6

| Test compounds (Number) | Concentration (ppm) | Infected Index | Phytotoxicity |
| --- | --- | --- | --- |
| 1 | 1,000 | 6.3 | Nil |
| 2 | 1,000 | 12.4 | Nil |
| 3 | 1,000 | 13.7 | Nil |
| 5 | 1,000 | 8.8 | Nil |
| 6 | 1,000 | 7.5 | Nil |
| 7 | 1,000 | 7.0 | Nil |
| 10 | 1,000 | 12.6 | Nil |
| 12 | 1,000 | 15.9 | Nil |
| 14 | 1,000 | 12.9 | Nil |
| 16 | 1,000 | 9.4 | Nil |
| 23 | 1,000 | 10.7 | Nil |
| 25 | 1,000 | 12.7 | Nil |
| 26 | 1,000 | 17.0 | Nil |
| 27 | 1,000 | 19.2 | Nil |
| 28 | 1,000 | 15.3 | Nil |
| 29 | 1,000 | 4.2 | Nil |
| 35 | 1,000 | 18.2 | Nil |
| Zineb (72% W.P.) | 1,440 | 16.4 | Nil |
| Untreated | — | 89.1 | — |

EXPERIMENTAL EXAMPLE 6

Exterminating test on storage disease of oranges caused by *Penicillium digitatum* and *Alternaria citri*

The mandarin oranges were washed with water and air-dried. Eighty percent wettable powder of the Composition Example 2 was diluted with water, and the oranges were dipped in this solution for 3 minutes, then air-dried. The oranges were inoculated by means of spray with spore suspension of *Penicillium digitatum* and *Alternaria citri* after injured, and then kept in a moist chamber at 25° C.

Seventy five percent wettable powder of 1,2-bis (3-methoxy carbonyl-2-thioureid) benzene (hereinafter referred as Thiophanatemethyl) was used as the standard chemicals.

Six days after the inoculation, degrees of attack by the pathogen were observed and the results were shown in Table 7 with percentage of average of diseased area.

Table 7

| Test compounds (ppm) | Concentration (ppm) | Percentage of average diseased area (%) | | Phytotoxicity |
| --- | --- | --- | --- | --- |
| | | Common green mold | Black rot | |
| 1 | 800 | 25.0 | 15.8 | Nil |
| 4 | 800 | 15.0 | 12.5 | Nil |
| 6 | 800 | 25.0 | 13.0 | Nil |
| 7 | 800 | 20.0 | 8.5 | Nil |
| Thiophanate methyl (70% W.P.) | 1,400 | 37.0 | 25.5 | Nil |
| Untreatem | — | 89.0 | 38.0 | — |

EXPERIMENTAL EXAMPLE 7

The test of killing fungi by seed treatment

Cucumber seeds (variety: Oyashma) were dipped in the spore suspension of *Cladosporium cucumerinum* and dried.

The seeds were dressed with 80% wettable powder obtained by Composition Example 2. On the other hand, other seeds were dipped in the aqueous solution of said wettable powder for 30 minutes. Five seeds dressed and 5 seeds dipped were placed on each separate potato dextrose agar plate. After 10 days after the treatment, degrees attacked by the pathogen were observed and the results were shown with an "Effective Index". An "Effective Index" was calculated as follows:

$$\text{Effective Index} = \frac{\text{Number of diseased seeds in untreated plot} - \text{Number of diseased seeds in treated plot}}{\text{Number of diseased seeds in untreated plot}}$$

Table 8

| Test Compounds (Number) | Method of treatment | The ratio of tested compounds per seeds or concentration of tested compound in the aqueous solution | Effective Index | Phytotoxicity |
| --- | --- | --- | --- | --- |
| 1 | dressed | 1 % | 88.3 | Nil |
| 6 | " | 1 % | 79.2 | Nil |
| 29 | " | 1 % | 80.4 | Nil |
| 1 | dipped | 5,000 ppm | 92.7 | Nil |
| 6 | " | 5,000 ppm | 85.8 | Nil |
| 29 | " | 5,000 ppm | 90.6 | Nil |
| Untreated | — | — | 0 | — |

We claim:

1. A compound represented by the formula $$\text{X—O} \underset{Y}{\underset{|}{\bigcirc}} \text{—S—}\overset{O}{\underset{\|}{C}}\text{—NH—}\bigcirc\text{—Zm}$$

where X represents a lower alkylsulfonyl, a lower alkoxycarbonyl, a N-lower alkylcarbamoyl, a lower alkylcarbonyl or an 0,0-di lower alkyl thiophosphonyl, Y represents hydrogen, chlorine, bromine or a lower alkyl, Z represents hydrogen fluorine, chlorine, bromine, a lower alkyl, a lower alkoxy or trifluoromethyl and m represents 1 or 2.

2. The compound according to claim 1 where X is an alkyl sulfonyl having from 1 to 3 carbon atoms, methoxy carbonyl, ethoxy carbonyl, acetyl or 0,0-dimethyl thiophosphonyl, Y is hydrogen or chlorine Z is hydrogen, p-fluorine, p-chlorine, p-bromine or methoxy and m is 1.

3. A fungicidal composition for agriculture comprising 1–95% of a compound of the formula $$\text{X—O} \underset{Y}{\underset{|}{\bigcirc}} \text{—S—}\overset{O}{\underset{\|}{C}}\text{—NH—}\bigcirc\text{—Zm}$$

where X represents a lower alkylsulfonyl, a lower alkoxycarbonyl, a N-lower alkylcarbamoyl, a lower alkylcarbonyl or an 0,0-dilower alkyl thiophosphonyl, Y represents hydrogen, chlorine, bromine and a lower alkyl, Z represents hydrogen fluorine, chlorine, bromine, a lower alkyl, a lower alkoxy or trifluoromethyl and m represents 1 or 2, and 99 – 5% (by weight) of adjuvants.

4. The fungicidal composition according to claim 3 wherein X is an alkyl sulfonyl having from 1 to 3 carbon atoms, methoxy carbonyl, ethoxy carbonyl, acetyl or 0,0-dimethylthiophosphonyl, Y is hydrogen or chlorine, Z is hydrogen, p-fluorine, p-chlorine, p-bormine or methoxy and m is 1.

5. A method for killing fungi which harm useful plants or crops characterized by applying to the fungi an effective amount of a compound of the formula

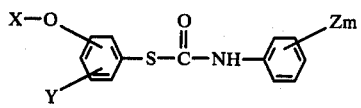

where X represents a lower alkylsulfonyl, a lower alkoxycarbonyl, a N-lower alkylcarbamoyl, a lower alkylcarbonyl or an 0,0-di lower alkyl thiophosphonyl, Y represents hydrogen, chlorine, bromine or a lower alkyl, Z represents hydrogen, fluorine, chlorine, bromine, a lower alkyl, a lower alkoxy or trifluorimethyl and $m$ represents 1 or 2.

6. The method according to claim 5 wherein X is an alkyl sulfonyl having from 1 to 3 carbon atoms, methoxy carbonyl, ethoxy carbonyl, acetyl or 0,0-dimethylthiophosphonyl, Y is hydrogen or chlorine, Z is hydrogen, p-fluorine, p-chlorine, p-bromine or methoxy and $m$ is 1.

* * * * *